United States Patent [19]
Gord et al.

[11] Patent Number: 5,999,848
[45] Date of Patent: Dec. 7, 1999

[54] DAISY CHAINABLE SENSORS AND STIMULATORS FOR IMPLANTATION IN LIVING TISSUE

[75] Inventors: John C. Gord, Venice; Joseph H. Schulman, Santa Clarita, both of Calif.

[73] Assignee: Alfred E. Mann Foundation, Valencia, Calif.

[21] Appl. No.: 08/928,867

[22] Filed: Sep. 12, 1997

[51] Int. Cl.$^6$ ................................................. A61N 1/00
[52] U.S. Cl. ............................................. 607/2; 607/60
[58] Field of Search ...................... 607/2, 6, 17–24, 607/32, 39–61; 600/300, 301; 128/903

[56] References Cited

U.S. PATENT DOCUMENTS

| | | | |
|---|---|---|---|
| 4,671,288 | 6/1987 | Gough | 128/635 |
| 4,877,032 | 10/1989 | Heinze et al. | 607/2 |
| 5,016,631 | 5/1991 | Hogrefe . | |
| 5,186,169 | 2/1993 | Schaldach . | |
| 5,324,316 | 6/1994 | Schulman et al. | 607/61 |
| 5,325,870 | 7/1994 | Kroll et al. . | |
| 5,358,514 | 10/1994 | Schulman et al. | 607/61 |
| 5,470,348 | 11/1995 | Neubauer et al. . | |
| 5,497,772 | 3/1996 | Schulman et al. | 128/635 |
| 5,571,148 | 11/1996 | Loeb et al. | 607/57 |
| 5,593,430 | 1/1997 | Renger | 607/18 |
| 5,603,726 | 2/1997 | Schulman et al. | 607/57 |
| 5,651,367 | 7/1997 | Schloemer et al. | 600/483 |

*Primary Examiner*—Jeffrey R. Jastrzab
*Attorney, Agent, or Firm*—Abraham N. Seidman

[57] ABSTRACT

An implantable sensor/stimulator is connectable to a controller using just two conductors, which two conductors carry both operating power and data (data commands and/or measured data) between the sensor/stimulator and control circuit. Each sensor/stimulator may be serially connected to another sensor/stimulator, again using only two conductors, thereby allowing a "daisy chain" of such sensors/stimulators to be formed. Each sensor/stimulator in the daisy chain is individually addressable by the control circuit. Input data is sent to the sensors over the two conductors using a phase-modulated biphasic modulation scheme, which scheme also provides operating power for each sensor/stimulator connected to the two conductors. Output data is sent from the sensors to the controller over the same two conductors using a pulse-position presence/absence modulation scheme. The data transmission schemes provide a very high signal-to-noise ratio. Each sensor/stimulator includes a power rectifier circuit, a line interface circuit, a state machine controller, at least one sensor that generates an analog output current as a function of a sensed parameter, a low power current-to-frequency converter circuit, and a counter circuit.

17 Claims, 7 Drawing Sheets

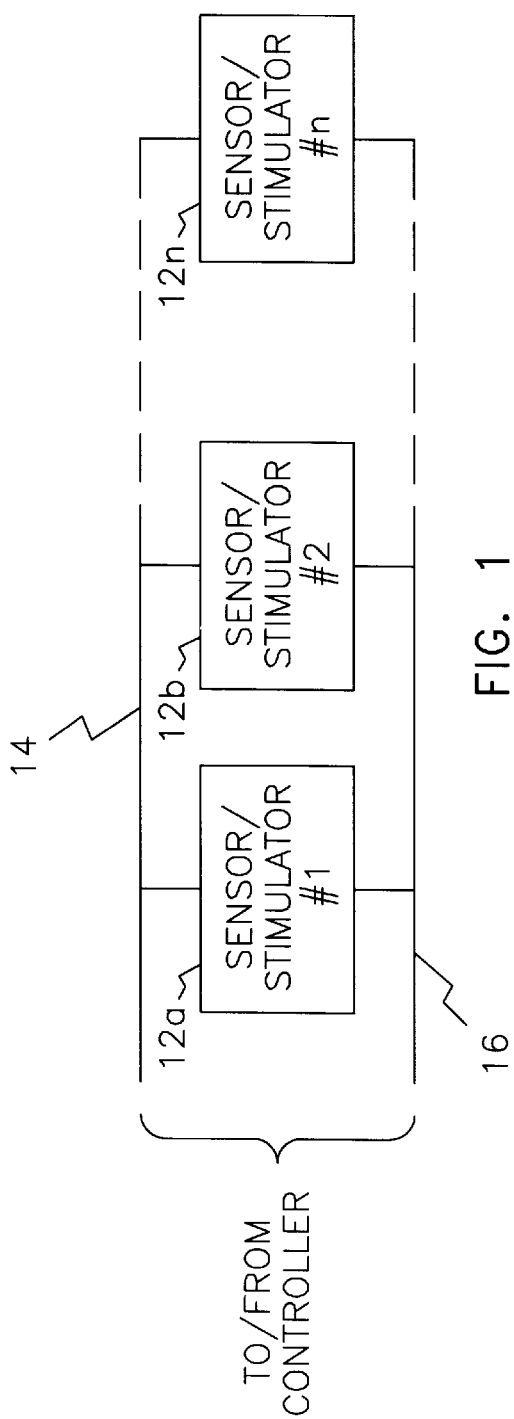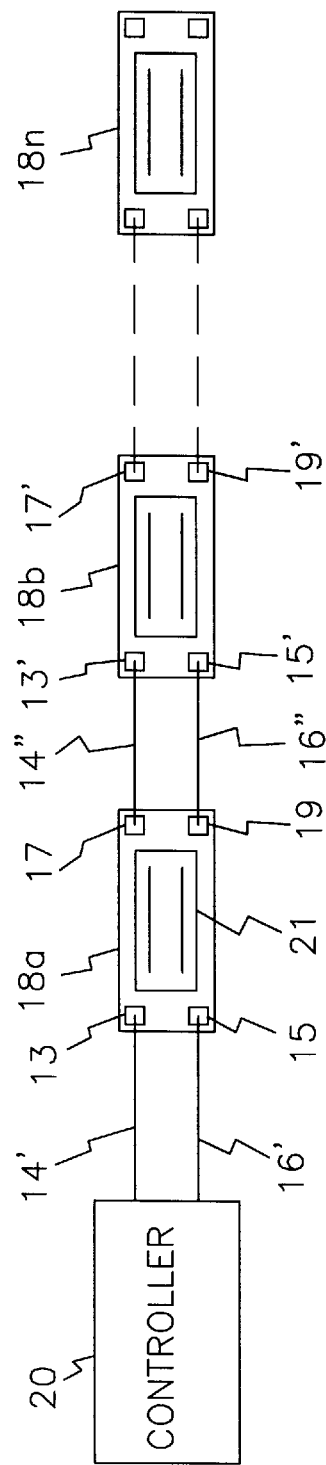

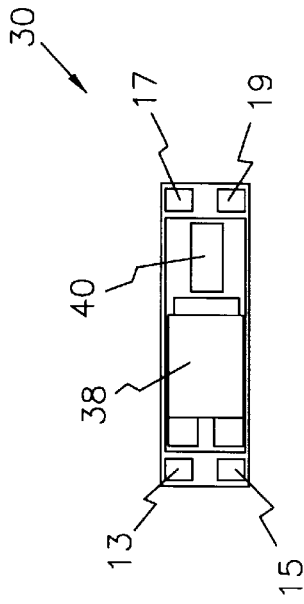
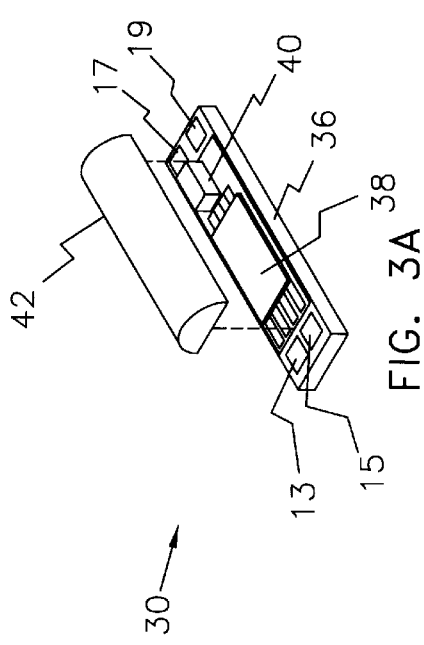
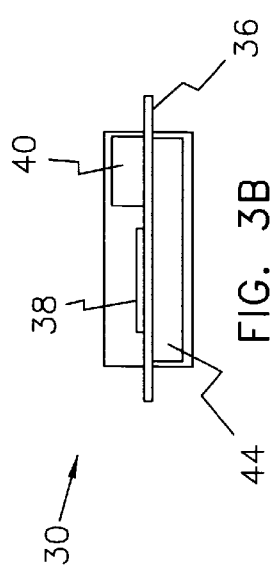
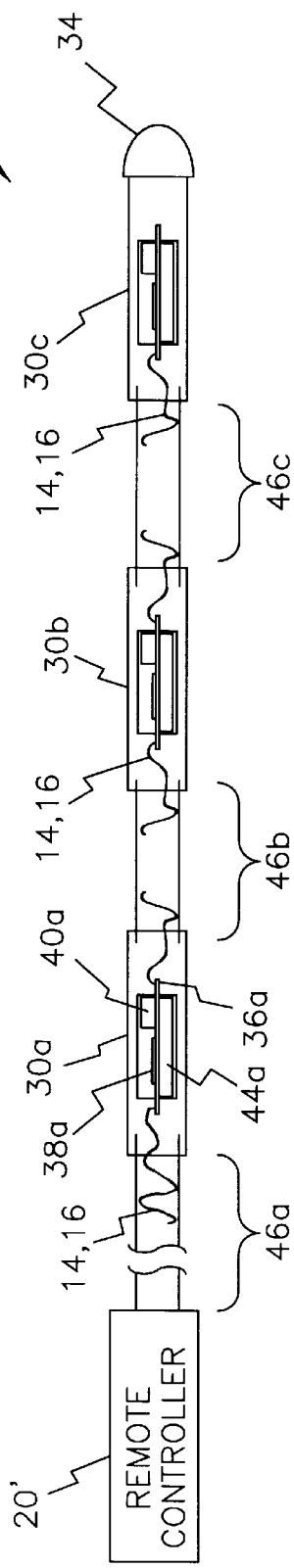

DAISY CHAINABLE SENSORS AND STIMULATORS FOR IMPLANTATION IN LIVING TISSUE

FIELD OF THE INVENTION

The present invention relates to implantable medical devices, and more particularly to very small implantable sensors and/or stimulators that may be serially connected in a daisy-chain using just two conductors. Important aspects of the invention relate to a very-low power rectifier circuit, line interface circuit, and current-to-frequency converter circuit that form part of each daisy-chainable implantable sensor/stimulator, which circuits facilitate the powering and operation of the implantable sensor/stimulator using just two conductors which are shared with all other sensors/stimulators in the daisy chain.

BACKGROUND OF THE INVENTION

In the implantable medical device field, a medical device, configured to perform a desired medical function, is implanted in the living tissue of a patient so that a desired function may be carried out as needed for the benefit of the patient. Numerous examples of implantable medical devices are known in the art, ranging from implantable pacemakers, cochlear stimulators, muscle stimulators, glucose sensors, and the like.

Many implantable medical devices are configured to perform only the stimulation function, i.e., to stimulate on command a prescribed muscle tissue in order cause the muscle to contract. An example of a tiny implantable stimulator is shown, e.g., in U.S. Pat. Nos. 5,324,316 or 5,358,514.

Other implantable medical devices are configured to perform only the sensing function, i.e., to sense a particular parameter, e.g., the amount of a specified substance in the blood or tissue of the patient, and to generate an electrical signal indicative of the quantity or concentration level of the substance sensed. Such electrical signal is then coupled to a suitable controller, which may or may not be implantable, and the controller responds to the sensed information in a way to enable the medical device to perform its intended function, e.g., to display and/or record the measurement of the sensed substance. An example of an implantable medical device that performs the sensing function is shown, e.g., in U.S. Pat. No. 4,671,288.

Still other implantable medical devices are configured to perform both the sensing and stimulating function. In such instances, the medical device typically includes separate sensing, stimulating and control circuits. The sensing circuit senses the presence or absence of a particular parameter or substance. The control circuit analyzes the information sensed by the sensor and determines whether a stimulation current pulse is needed. If a stimulation current pulse is needed, the control circuit directs the stimulating circuit to provide a specified stimulation current pulse. A pacemaker is a classic example of an implantable medical device that performs both the sensing function (sensing whether the heart needs to be stimulated and at what rate) and the stimulating function (stimulating the heart as needed to maintain a desired heart rhythm).

As medical devices have become more sophisticated, there is a continual need to use more than one sensor. For example, in some instances, more than one sensor is needed to measure more than one substance or physiological parameter. In other instances, more than one sensor may be needed to measure or sense the same substance or physiological parameter at different locations within the patient's body. Similarly, depending upon the medical application involved, there may be a need to stimulate muscle tissue at more than one location in the body. One way of providing stimulation at multiple locations is to implant separate stimulators at each desired location and then to coordinate the operation of the stimulators so as to provide a desired result. See, e.g., U.S. Pat. No. 5,571,148.

Whenever multiple sensors and/or multiple stimulators are implanted and are intended to be used in concert to achieve a desired medical function, there is a need to connect or couple such separate multiple sensors/stimulators to a single control circuit or common control point. Sometimes the control function is performed external to the patient, in which case the sensors/stimulators are connected to an implanted telemetry circuit or equivalent; or, alternatively, a telemetry circuit is included as part of each sensor that allows data and commands to be sent, transferred, or otherwise coupled across the tissue/skin of the patient between an external control device and the implanted sensor/stimulator. At other times, the control function is performed by an implantable control circuit, usually connected directly to the implanted sensors/stimulators. When an implanted control circuit is used, it usually includes a telemetry circuit, or equivalent circuit, that allows the implanted control circuit to communicate with an external programmer, thereby allowing the implanted control circuit to be programmed, or otherwise modified and/or monitored, by the external programmer.

When multiple sensors/stimulators are used, several problems must be addressed. For example, unless each of the multiple sensors/stimulators are connected to a common controller and/or telemetry circuit, each sensor/stimulator must employ its own telemetry circuit, or equivalent circuit, that allows it to be monitored and/or controlled. Such individual telemetry or communication circuits may add undue complexity to the implanted sensors/stimulators, increasing the size, weight and/or power consumption of the sensors. What is needed are relatively simple sensors and stimulators that may be implanted at multiple locations within the patient, yet operate independent of each other in an efficient and effective manner.

When multiple sensors/stimulators are directly monitored and/or controlled by a control circuit, there must be a direct connection, i.e., at least a separate conductor and a return path, for each sensor/stimulator. If the number of sensors/stimulators is large, the number of separate conductors that are required to control and/or monitor such sensors/stimulators can become unwieldy. The number of conductors can become especially large and difficult to manage when each sensor requires more than two conductors, e.g., as when each sensor performs multiple functions, requiring a separate output conductor for each function, in addition to conductors to carry power to the sensor. Moreover, the output signal from many sensors, i.e., the signal that provides a measure of the parameter or substance being monitored or sensed, is typically a very low level analog signal that cannot be transmitted over very long distances without amplification or buffering. That is, such low level signals are easily corrupted with noise, particularly when the conductors are placed in a very hostile environment (e.g., within living tissue, which is equivalent to being immersed in salt water). Low level signals in a hostile environment result in a signal-to-noise (S/N) ratio that is unacceptably low. An unacceptably low S/N ratio, in turn, dictates that signal amplification and/or special buffering circuits be employed. Such signal amplification and/or buffering, however, disadvantageously require additional circuitry, thereby increasing the complexity, size and weight of the device, and further require additional operating power. What is clearly needed, therefore, are sensors/stimulators that can be readily operated in a multiple sensor/stimulator configuration, yet require a minimum number of conductors to connect the sensors/stimulators to a control circuit, and wherein a high S/N ratio can be maintained for data and command signals that are transmitted to and from the sensors/stimulators.

SUMMARY OF THE INVENTION

The present invention addresses the above and other needs by providing an implantable medical device, e.g., a sensor/stimulator, that can be connected to a controller, typically an implantable controller (or an implantable transceiver that is in communication with an external controller), using just two conductors that carry both operating power and data (data commands and/or measured data) between the device and control circuit. Moreover, a plurality of such devices may be connected together using just two conductors. That is, a first device may be connected to the controller using just two conductors. Another device, using the same two conductors as are connected to the first device, may then be connected to the first device, thereby allowing a "daisy chain" of such devices to be formed. Advantageously, each device in the daisy chain is individually addressable by the control circuit, and the manner in which data is transmitted between a given device and the control circuit is very immune to noise, thereby providing a very high S/N ratio.

In accordance with one aspect of the invention, the invention comprises a medical device having an hermetically sealed part containing electrical circuitry and a non-hermetically sealed part. The non-hermetically sealed part includes a first pair of terminals and a second pair of terminals. The first pair of terminals function as the input/output terminals for connecting a first medical device to a controller using just two conductors, one conductor being connected to each terminal. The second pair of terminals function as connection terminals for attaching an additional medical device to the first medical device. The input/output terminals of an additional medical device may then be connected to the controller by simply connecting respective conductors between the connection terminals of the medical device already connected to the controller and the input/output terminals of the additional medical device. In this fashion, a daisy-chain of such medical devices may be formed.

In one embodiment, the first pair of terminals is electrically connected to the second pair of terminals through feed-through means that make the desired electrical connection through the hermetically sealed part. In such embodiment, the first feed-through means make electrical contact between each terminal of the first pair of terminals and a respective portion of the electrical circuitry within the hermetically sealed part. Then, second feed-through means make electrical contact with the respective portions of the electrical circuitry within the hermetically sealed part and the second pair of terminals so that a direct electrical connection is established between corresponding terminals of the first and second pair of terminals. Thus, the first pair of terminals, or input/output terminals, comprises a means for applying electrical power and data to the electrical circuitry within the hermetically sealed part, as well as a means for receiving data from the electrical circuitry within the hermetically sealed part; and the second pair of terminals, or connection terminals, comprises a means for passing the electrical power and data received on the first pair of terminals to a corresponding first pair of terminals of another implantable medical device.

In another embodiment, the first pair of terminals may be connected to the second pair of terminals directly within or on the non-hermetically sealed part without passing through the hermetically sealed part. Hence, in this embodiment, only one set of feed-through means need be employed to connect the first and second pairs of terminals to the respective portions of the electrical circuitry within the hermetically sealed part.

In either embodiment, it is a feature of the invention to allow a plurality of such implantable medical devices to be daisy-chained together by simply connecting a pair of conductors between the second pair of terminals of one implantable medical device and the first pair of terminals of another implantable medical device.

In accordance with another aspect of the invention, the medical device comprises an implantable sensor/stimulator device adapted for implantation in living tissue, and particularly adapted to sense a desired physiological parameter or function, e.g., to sense the glucose level of a patient, and/or to stimulate selected tissue with an electrical shock. Such implantable sensor/stimulator includes: (1) a carrier having first and second pads thereon to which first and second line conductors may be attached; (2) a low power rectifier circuit carried by the carrier and connected to the first and second pads, with the rectifier circuit including means for generating an operating voltage from biphasic pulses applied across the first and second pads; (3) a line interface circuit carried by the carrier and connected to the first and second pads; (4) a sensor that senses a specified parameter or substance and generates an analog output signal which varies as a function of how much of the specified parameter or substance is sensed; (5) a converter circuit that converts the analog output signal from the sensor to a digital sensor signal comprised of a multiplicity of respective bits; (6) state machine means that defines address data corresponding to the implantable sensor/stimulator, and that receives detected data from the line interface circuit and determines if the detected data corresponds to the defined address data of the implantable sensor/stimulator, and if so, responding thereto by applying the digital sensor signal to the line interface circuit so that it can be transmitted to the first and second line conductors attached to the first and second pads; and (7) means for hermetically sealing the rectifier circuit, line interface circuit, converter circuit, and state machine means.

In such embodiment, the line interface circuit includes a detecting means for serially detecting whether input biphasic pulses applied across the first and second pads are of a first phase or a second phase, a first phase corresponding to a received data bit representing a binary "1", and a second phase corresponding to a received data bit representing a binary "0". In this manner, an input data stream may be received by the line interface circuit from biphasic data pulses that are applied between the first and second line conductors, i.e., between the first and second pads attached to the first and second line conductors.

The line interface circuit also includes transmission means for serially applying an output pulse, e.g., a monophasic or preferably biphasic pulse, having a first or second amplitude across the first and second pads at a time in-between when the input biphasic pulses are applied across the first and second pads, where a first amplitude, e.g., a maximum amplitude, of the output pulse represents a binary "1", and a second amplitude, e.g., a minimum or even a zero amplitude (i.e., the absence of a pulse) of the output pulse represents a binary "0". In this way, an output data stream may be transmitted by the line interface circuit onto the first and second pads, and hence, onto the first and second line conductors attached to the first and second pads.

Advantageously, by using biphasic pulses in the manner described, such pulses serve a dual purpose:

(1) the energy contained therein may be rectified by the rectifier circuit and used to power the device, and (2) the information contained therein may be detected and provide a stream of input or control data to the device. Further, by interleaving amplitude modulated output pulses inbetween the incoming biphasic pulses, output data sensed or generated by the device may be transmitted on the same first and second line conductors used to send an input data stream to the device. Significantly, when the absence of a monophasic pulse is used to signify one binary state, e.g., a binary "0", and an output pulse of maximum amplitude is used to signify another binary state, e.g., a binary "1", a high signal-to-noise ratio may be achieved, allowing the output data to be transmitted over a minimum number of conductors (two conductors) in a very noisy environment.

It is thus a feature of the present invention to provide a means whereby implantable sensors or stimulators may be daisy chained together using a minimum number of connecting conductors.

It is an additional feature of the invention to provide a daisy chain of implantable sensor/stimulator devices, serially connected together through a common power/data bus, wherein each individual device is addressable from a common controller unit connected by way of the common power/data bus to each of the implantable devices.

It is another feature of the invention to provide individual implantable sensors and/or stimulators that can transmit and/or receive power and data signals over a minimum number of signal lines connected therebetween.

It is yet another feature of the invention to provide an implantable sensor/stimulator device having an hermetically sealed part and a non-hermetically sealed part, with electrical feed-through means for making electrical connections between the hermetically sealed part and the non-hermetically sealed part, and wherein the hermetically sealed part encompasses electrical circuits for operating and controlling the device, and further wherein the non-hermetically sealed part includes a sensor for sensing a condition or substance to which the device is exposed, electrical terminals or pads to which connecting conductors may be connected, and/or electrodes through which stimulating current pulses may be applied to surrounding tissue or body fluids.

BRIEF DESCRIPTION OF THE DRAWINGS

The above and other aspects, features and advantages of the present invention will be more apparent from the following more particular description thereof, presented in conjunction with the following drawings wherein:

FIG. 1 is a block diagram that illustrates multiple sensors/stimulators connected together using a two-conductor bus, which two-conductor bus may be connected to a controller;

FIG. 2 schematically illustrates a preferred manner of how a sensor/stimulator made in accordance with the present invention may be connected with a controller and other sensors/stimulators in a serial or daisy-chain fashion;

FIG. 3A shows a perspective, partially exploded, view of a preferred sensor/stimulator of the type used in the daisy chain of FIG. 2;

FIG. 3B illustrates a sectional side view of the sensor/stimulator of FIG. 3A;

FIG. 3C illustrates a sectional top view of the sensor/stimulator of FIG. 3A;

FIG. 3D illustrates a sectional end view of the sensor/stimulator of FIG. 3A;

FIG. 4 depicts an implantable lead that includes a plurality of the sensors/stimulators of FIGS. 3A–3D;

Corresponding reference characters indicate corresponding components throughout the several views of the drawings.

DETAILED DESCRIPTION OF THE INVENTION

Figure 5A:
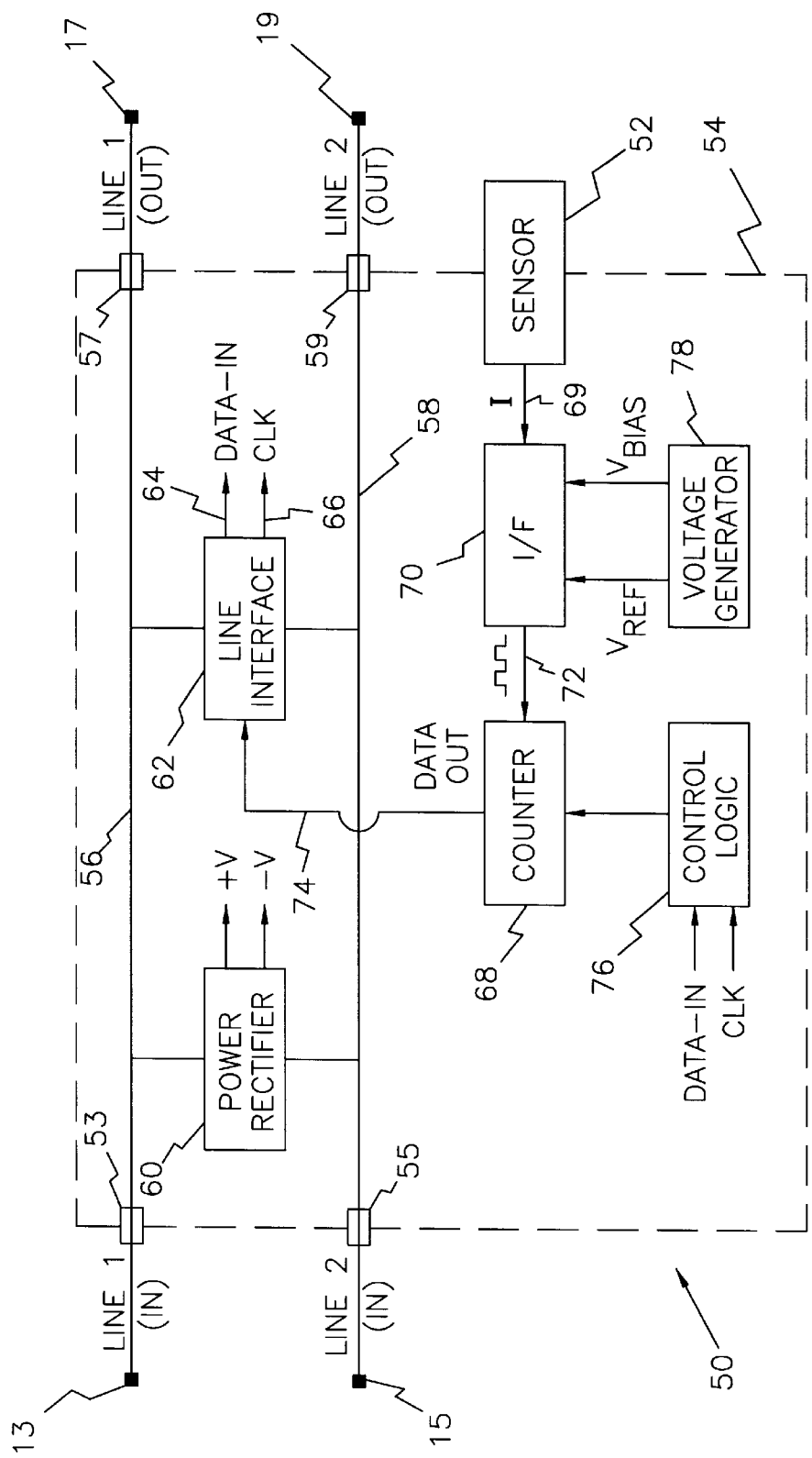
FIG. 5A is a functional block diagram of a simple daisy-chainable implantable device made in accordance with the present invention wherein an electrical path for attaching additional devices passes through an hermetically-sealed portion of the implantable device.

The following description is of the best mode presently contemplated for carrying out the invention. This description is not to be taken in a limiting sense, but is made merely for the purpose of describing the general principles of the invention. The scope of the invention should be determined with reference to the claims.

Turning first to FIG. 1, a block diagram is shown that illustrates multiple sensors/stimulators 12a, 12b, . . . 12n, or other implantable devices, connected together, as well as a controller (not shown) using just two common conductors 14 and 16. The two conductors 14 and 16 provide a common signal and return for data signals and power signals that are sent from the controller to the devices 12a, 12b, . . . 12n, as well as a common signal and return path for data signals transmitted from the devices 12a, 12b, . . . 12n, to the controller.

FIG. 2 schematically illustrates how an implantable device, e.g., a sensor/stimulator 18a, made in accordance with the present invention may be connected with a remote controller 20 and other implantable devices 18b, . . . 18n, in a serial or daisy-chain fashion. As seen in FIG. 2, the device 18a is connected to the controller 20 by two conductors 14' and 16' which are attached to a first pair of pads or terminals 13 and 15 along a proximal side (i.e, the side closest to the controller 20) of the device 18a. Another pair of pads or terminals 17 and 19 are located along a distal side (i.e., the side farthest from the controller 20) of the device 18a. As will become evident from the description that follows, the distal pad 17 is electrically connected to the proximal pad 13 through the circuitry 21 located on the device 18a. Similarly, the distal pad 19 is electrically connected to the proximal pad 15 through the circuitry 21 included within the device 18a. Two additional conductors 14" and 16" are then used to connect the distal pads 17 and 19 of the device 18a to corresponding proximal pads 13' and 15' of the next device 18b connected in the daisy chain. In this manner, as many devices as desired may be serially connected to the controlled using just two conductors.

It is noted that the FIG. 1 is functionally electrically equivalent to FIG. 2. FIG. 2 simply employs proximal and distal pairs of pads or terminals to facilitate the connection of additional devices to the chain by extending two conductors from the distal pads 17 and 19 of a more proximal device in the chain to the proximal pads 13' and 15' of a new device to be added to the chain. However, where the particular application allows connections to be made, or branched off of, the two main conductors 14 and 16, then the configuration of FIG. 1 may be used just as well as the configuration of FIG. 2.

There exist many different applications for the daisy-chainable sensor/stimulators 12 or 18 of the present invention illustrated in FIGS. 1 or 2. Generally, where the sensor/stimulators 12 or 18 are implanted, they are designed to sense one or more body parameters or substances found in body tissue or fluids, e.g., glucose level, blood pH, $O_2$, temperature, or the like. Such measurements can provide valuable information regarding the condition and status of the patient. As such, it is ofttimes desirable to make more than one measurement within the same general body tissue area so as to be able to compute an average or mean of the measurements thus made, or otherwise obtain a consensus from several different readings, thereby better assuring the accuracy and reliability of the data thus gathered.

Other times, it may be desirable to obtain various measurements of a given substance at physically-related, but different, body locations. For example, for some applications, e.g., a closed-loop insulin infusion system, it could be advantageous to obtain a glucose reading within the blood stream and another glucose reading within the body tissue adjacent the blood stream. This is because the time constant associated with how rapidly one glucose reading changes compared with the other may be different (and, in fact, is usually different), and being able to obtain or monitor such difference would provide valuable information regarding the regulation of the insulin infusion.

Turning next to FIGS. 3A, 3B, 3C and 3D, there are shown, respectively, a perspective exploded view (FIG. 3A), a side view (FIG. 3B), a top view (FIG. 3C), and an end view (FIG. 3D), of a typical implantable sensor device 30 of a type suited for use with the present invention. As seen best in FIG. 3A, the sensor device 30 typically includes a carrier or substrate 36 on which an integrated circuit (IC) 38 and other components, such as a capacitor 40, are mounted. In some embodiments, it should be noted that the carrier or substrate 36 may actually comprise the substrate on which the IC 38 is fabricated; but for purposes of the explanation which follows, it is assumed that a separate substrate or carrier 36 is employed with various circuit elements mounted thereon to form a hybrid circuit. The carrier or substrate has conductive patterns etched or otherwise deposited thereon to interconnect the IC 30, capacitor 40, and any other components to form a hybrid circuit which carries out the desired sensing (or other) function.

All of the components of the hybrid circuit are hermetically sealed within a cavity formed by a lid or cover 42 which is bonded to the substrate 36. Proximal pads or terminals 13 and 15, as well as distal pads or terminals 17 and 19, remain outside of the hermetically sealed part of the hybrid circuit created by the cover 42. These proximal and distal pads, however, are electrically connected to the circuitry within the hermetically sealed part through suitable feedthrough connections. While any suitable feedthrough connection may be used for this purpose, a preferred manner of making such feedthrough connection is to use a feedthru connection that passes through the carrier or substrate in the stair-step manner (including both vertical and horizontal segments) disclosed in U.S. patent application Ser. No. 08/515,559, filed Aug. 16, 1995, now U.S. Pat. No. 5,750,926, entitled "Hermetically-Sealed Electrical Feedthrough For Use With Implantable Electronic Devices", which application is assigned to the same assignee as is the instant application, and which application is incorporated herein by reference.

On the side of the carrier or substrate opposite the hybrid electrical circuitry, a suitable electrochemical sensor 44, or other desired type of sensor or stimulator, may be formed or located. A type of electrochemical sensor that may be used, for example, is the enzyme electrode sensor described in U.S. Pat. No. 5,497,772, incorporated herein by reference, and in particular, in FIGS. 2A, 2B, 2C, 3, 4A and 4B of that patent. However, it is to be emphasized that the precise nature of the sensor 44, or other implantable element used within the device 30, is not critical to the present invention. All that matters is that the sensor or other element be implantable, and that it provide a desired function, e.g., sense a certain type of parameter of substance, or generate a certain type of signal, in response to an appropriate control signal or signals.

Whatever, type of control signal(s) or output signal(s) is/are generated by the sensor 44, or other element, such signal(s) may be communicated from the hybrid circuit side of the substrate or carrier 36 (which is the top side as the device 30 is oriented in FIG. 3B or FIG. 3D, and which top side includes the hermetically sealed portion of the device) to the sensor side of the device 30 (which is the bottom side as shown in FIG. 3B or 3D) by way of appropriate hermetically-sealed feedthroughs that pass step-wise from the hybrid (top) side of the device 30 through the substrate or carrier, e.g., in the manner set forth in the above-referenced '559 patent application, to the sensor (bottom) side of the device 30.

For example, where the sensor comprises a glucose sensor of the type taught in U.S. Pat. No. 5,497,772, there may be five conductors that electrically interface with the main elements (electrodes) of the sensor, as seen best in FIG. 4A of the '772 patent. Where such a glucose sensor is employed, these five conductors thus interface with the hybrid electrical circuitry found on the top side of the carrier 36) using appropriate feedthroughs that hermetically pass step-wise through the carrier 36, i.e., that pass through the carrier using both vertical and horizontal segments, as taught in the '559 application.

It is to be emphasized that the invention is not limited to the specific sensor configuration shown in FIGS. 3A–3D. Rather, any type of implantable device, whether configured as illustrated in FIGS. 3A–3D or otherwise, could be used with the invention. The present invention relates to the manner in which multiple sensors, or other implantable devices, regardless of their shape or configuration, may be serially connected in daisy-chain fashion using a minimum number of conductors, e.g., two conductors, as well as to the manner in which such devices electrically communicate with the controller 20 or other remote device so that each is individually addressable by the controller, and so that each can send data to the controller. Other aspects and features of such invention, e.g., the manner in which some of the circuitry contained within the hermetically-sealed portion of the sensor device 30 operate so as to consume very low power, are the subject of separate applications filed concurrently herewith. Such concurrently-filed and pending applications, assigned to the same assignee as the present application, include: (1) A LOW POWER CURRENT-TO-FREQUENCY CONVERTER FOR USE IN IMPLANTABLE SENSORS (Attorney Docket No. 57794), Ser. No. 08/928,868, filed Sep. 12, 1997; and (2) A LOW POWER RECTIFIER CIRCUIT (Attorney Docket No. 57795), Ser. No. 08/928,871, filed Sep. 12, 1997; which applications are expressly incorporated herein by reference.

It is noted that the configuration of FIG. 2 is especially well-suited where several of the implantable devices are to be daisy-chained together to form a single lead 32, as shown in FIG. 4. As seen in FIG. 4, three sensor-type devices 30a, 30b, and 30c are connected together via lead segments 46a, 46b, and 46c. Each of the lead segments 46a, 46b, and 46c, contain two conductors 14, 16, and may be constructed in any suitable manner, e.g., with the two conductors being spirally wound within the lead segments, and with the spiral windings being encased or covered within a sheath of silicone rubber, as is known in the lead art. (Note, that for purposes of FIG. 4 each of the two conductors 14, 16 within the lead 32 is considered as one conductor, even though each is segmented within the individual lead segments 46a, 46b and 46c as it connects from the distal pad of one device to the proximal pad of another device.) A distal cap 34 covers the distal pads of the end, or most-distal, device 30c of the lead 32.

As was mentioned above, it is noted that the device 30 need not necessarily employ a carrier 36, per se, as shown in FIGS. 3A, 3B, 3C, 3D and FIG. 4, wherein the control electronics are positioned on one side (the top side) of the carrier 36, and the sensor, or other device being used with or controlled by the electronics is placed on the other side (the bottom side) of the carrier. Rather, a ceramic or other substrate on which the IC 38 is formed may itself function as the carrier. That is, the vias that are formed in a substrate, or between various layers of an integrated circuit as the integrated circuit (IC) is formed, may function as hermetic feedthroughs, with selected layers and traces being coated as needed with aluminum oxide, or other oxide coatings, in the manner taught in the aforementioned '559 patent application, and/or in U.S. provisional application Ser. No. 60/033,637, filed Dec. 20, 1996 (Attorney Docket No. 57720), incorporated herein by reference, in order to seal appropriate sections or portions of the IC so that the coated IC may itself be implanted. In such embodiment, the sensor or other implantable element 44 used with or controlled by the IC may be formed on the back side of the IC's substrate. Thus, a carrier, per se, is not needed because the IC substrate functions as the carrier.

An important feature of the present invention is the electrical circuitry contained within or included as a part of what is referred to above as the "hybrid circuit portion" of the implantable device 30. The purpose of this electrical circuitry is to allow the implantable device 30 to be daisy chained with other similar implantable devices, while still allowing each individual device to be individually addressed, controlled and monitored from a single controller 20. This electrical circuitry, frequently referred to hereafter as the interface/control circuitry, is shown in FIGS. 3A, 3B, 3C, 3D and 4 as being located on the "top" side of the carrier 36, predominantly underneath the cover 42 in an hermetically sealed portion of the device 30. It is to be understood, however, that the location of the interface/control circuitry within the device 30 is not critical so long as it is appropriately hermetically sealed.

Figure 5B:
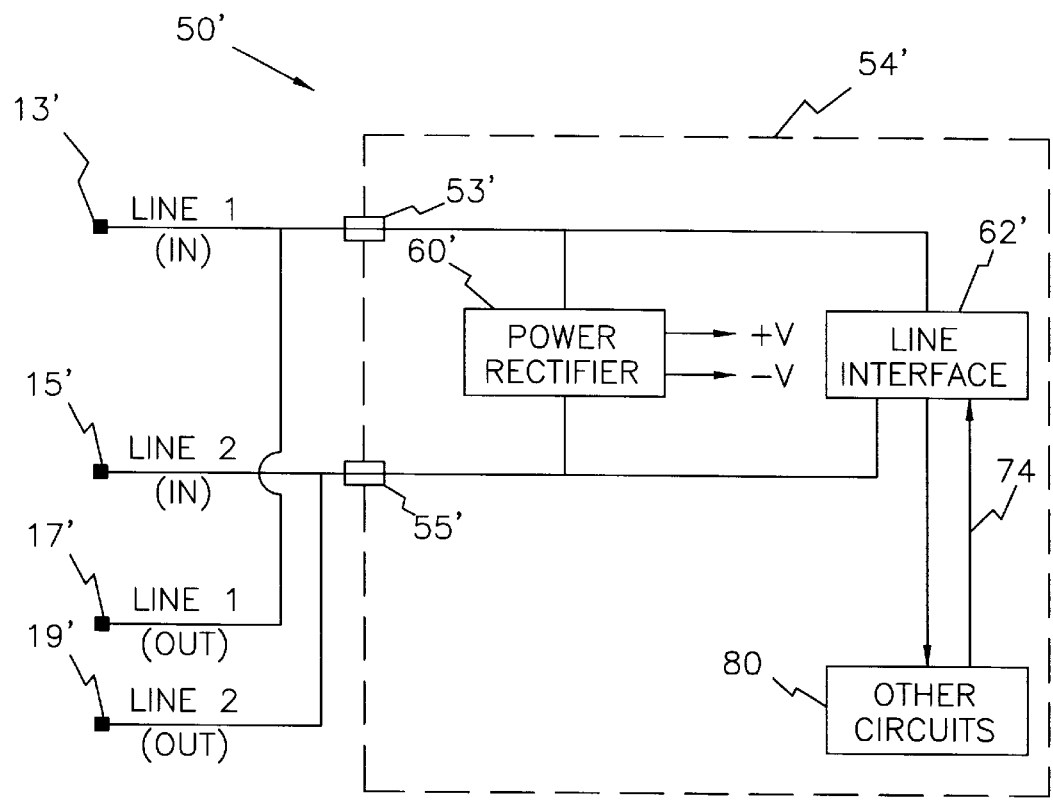
FIG. 5B is a functional block diagram as in FIG. 5A, but wherein the electrical path for attaching additional devices by-passes the hermetically-sealed portion of the implantable device.
Figure 5C:
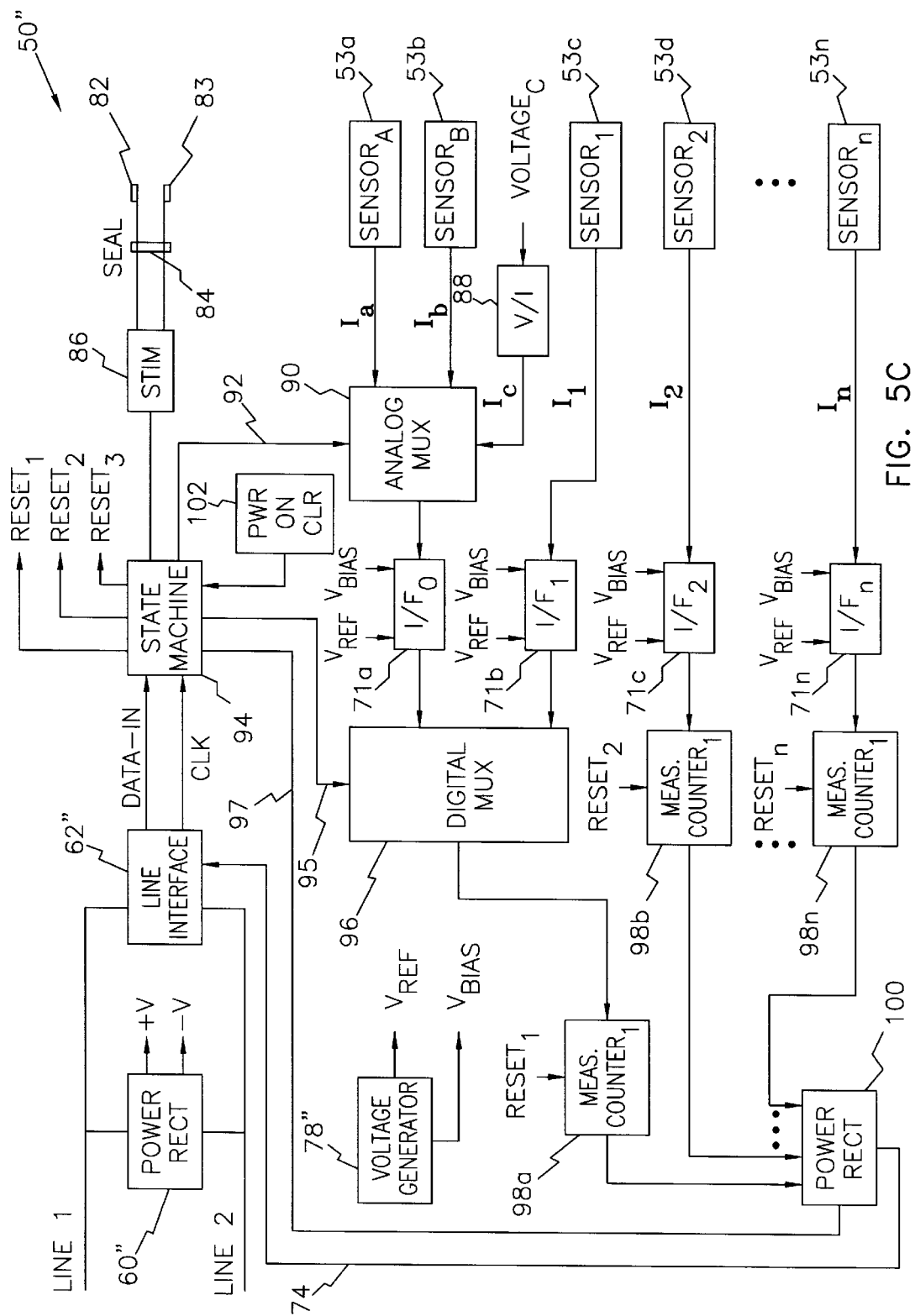
FIG. 5C is a functional block diagram as in FIG. 5A, but wherein additional circuit functions are provided so that a wide variety of different sensors and a stimulator may be included within the daisy-chainable implantable device.

The control/interface circuitry may take many and varied forms. FIGS. 5A, 5B and 5C, discussed below, show three such variations. Turning first to FIG. 5A, for example, a functional block diagram of a basic configuration of control/interface circuitry 50 for use with a single sensor 52 made in accordance with the present invention is shown. The dotted line 54 represents an hermetic seal that hermetically seals the circuitry 50 and all but a portion of the sensor 52. (Generally, where a sensor is employed, at least a portion of the sensor, e.g., an electrode, is left exposed to the tissue and fluids within which the device is implanted so that the sensor can perform its intended function of sensing some parameter or element present within the tissue and/or fluids.) The input pads 13 and 15, as well as the output pads 17 and 19, are not hermetically sealed, thereby allowing these pads to be readily connected to the two conductors 14 and 16 (FIG. 1) from the controller 20.

As seen in FIG. 5A, pads 13 and 15 are connected to respective conductive traces, labeled LINE 1 (IN) and LINE 2 (IN), and each of these conductive traces passes through respective feedthroughs 53 and 55 into the hermetically sealed portion of the circuitry 50. Pads 17 and 19, on the other side of the circuit, are likewise connected to respective conductive traces, labeled LINE 1 (OUT) and LINE 2 (OUT), and each of these conductive traces passes through respective feedthroughs 57 and 59 into the hermetically sealed portion 54 of the circuitry 50. Inside the hermetically sealed portion, LINE 1 (IN) connects with LINE 1 (OUT) via conductive trace 56, and LINE 2 (IN) connects with LINE 2 (OUT) via conductive trace 58. In this manner, pad 13 is electrically connected with pad 17 via trace 56 which passes through the hermetically sealed portion 54 between feedthroughs 53 and 57. This interconnection of pad 13, trace 56 and pad 57 may be referred to simply as LINE 1. similarly, pad 15 is electrically connected with pad 19 via trace 58, which trace also passes through the hermetically sealed portion 54 between feedthroughs 55 and 59. This interconnection may be referred to simply as LINE 2.

As seen in FIG. 5A, a power rectifier circuit 60 is connected between LINE 1 and LINE 2. This circuit extracts and rectifies any signal pulses found on LINE 1 and LINE 2 and produces an operating voltage, +V and −V, for powering the circuitry 50. Such rectification is not a trivial task given the low level signals which are generally present on LINE 1 and LINE 2, and given the fact that initially (in the absence of a signal to be rectified), there is no power yet available with which to operate the rectifier circuit. Details of such circuitry may be found in applicant's copending patent application Ser. No. 08/928,871, filed Sep. 12, 1997, A LOW POWER RECTIFIER CIRCUIT (Attorney Docket No. 57795), previously incorporated herein by reference.

A line interface circuit 62 also is connected between LINE 1 and LINE 2. The circuit 62 functions as an interface between the circuitry 50 and LINE 1 and LINE 2. To this end, the interface circuit 50 receives incoming data pulses present on LINE 1/LINE 2 and generates a DATA-IN signal on line 64 therefrom. The interface circuit 62 further generates a clock (CLK) signal on line 66 that is synchronized with the incoming data signals. The interface circuit 50 also receives digital output data, DATA OUT, from a counter circuit 68, and converts this output data to an appropriate format prior to placing the output data back on LINE 1/LINE 2. One type of line interface circuit 62 that may be used with the circuitry 50 is illustrated in the schematic diagram shown and explained below in conjunction with FIG. 9.

Still referring to FIG. 5A, the sensor 52 may be any suitable implantable sensor adapted to sense a desired condition, parameter, or substance present (or absent) in the implantable tissue within which the device 30 is implanted. For example, the sensor 52 may comprise a glucose sensor that generates an output analog current, I, appearing on line 69, having a magnitude that varies as a function of the sensed glucose.

As a practical matter, regardless of the type of sensor 52 that is employed, it will usually generate either an analog output voltage or an analog output current as a function of the concentration, magnitude, composition, or other attribute, of the parameter being sensed. Such analog current or voltage may then be converted, using an appropriate converter circuit, to a form that is more suitable for transmission.

While many different types of converter circuits may be employed, e.g., analog-to-digital (A/D) circuits as are known in the art, a preferred type of converter circuit is a voltage-to-frequency (V/F) converter or a current-to-frequency (I/F) converter, which converts a low level input signal (voltage or current) to a frequency signal. Such frequency signal appears on line 72. Typically, the frequency signal on line 72 comprises a train of pulses having a frequency (or repetition rate) that varies as a function of the input voltage or current. In FIG. 5A, for example, it is assumed that the sensor 52 generates an output current I, and that the converter circuit 70 comprises a current-to-frequency (I/F) converter circuit, generating an output pulse train on line 72 that has a frequency which varies as the magnitude of the current I varies. (Of course, it would be just as feasible for the sensor to generate an output voltage V, and have the converter circuit 70 comprise a voltage-to-frequency (V/F) converter circuit, generating an output pulse train on line 72 having a frequency that varies as the magnitude of the voltage V varies.)

Once a pulse train 72, or other ac signal, is generated having a frequency which varies as a function of the parameter being sensed by the sensor 52, such signal is applied to a counter circuit 68. (Note, as a shorthand notation used in this application, a signal appearing on signal line having a given reference number may be referred to as the signal having such given reference number, i.e., the signal appearing on signal line 72 may simply be referred to as "signal 72".) The counter circuit simply counts the number of pulses present in the signal 72 over a prescribed period of time, thereby providing a measure of the frequency of the signal 72. For example, if the signal 72 comprises a signal having 100 pulses per second (pps), and if the counter 68 is set to count the pulses over a period of time, or time-measurement window, of one second, then the counter 68, assuming it is reset to zero at the beginning of the measurement period, will have a count of 100 stored therein at the end of the measurement period. If the frequency of the signal 72 increases, e.g., to 120 pps, then the count held in the counter should increase to 120 at the end of the measurement period. If the frequency of the signal 72 decreases, e.g., to 80 pps, then the count held in the counter should decrease to 80 at the end of the measurement period. In this manner, by resetting the counter 68 at the beginning of each measurement period, the count held in the counter at the end of the measurement period provides a signal representative of the frequency of the signal 72. Such count signal, for the basic embodiment shown in FIG. 5A, may thus serve as the output data signal, DATA OUT, that is sent to the line interface circuit 62 over signal line 74.

Control of the counter 68, i.e., resetting the counter and/or stopping the counter after a prescribed measurement period, is controlled by control logic 76. In a simple embodiment, the measurement period may be a fixed time period. In other embodiments, the measurement period may be set by input data received over signal line 64 from the line interface circuit 62. The clock signal 66 may be used as a measure of elapsed time, as well as to coordinate when the counter 68 sends its DATA OUT signal 74 to the line interface circuit 62.

As needed, a voltage generator circuit 78 generates a reference voltage $V_{REF}$, and a bias signal, $V_{BIAS}$, that are used by the current-to-frequency (I/F) converter circuit 70 as it performs its function of converting the analog current signal 69 to a frequency signal 72, as explained more fully in the above-referenced copending patent application Ser. No. 08/928,868 A LOW POWER CURRENT-TO-FREQUENCY CONVERTER FOR USE IN IMPLANTABLE SENSORS, Attorney Docket No. 57794, previously incorporated herein by reference.

Turning next to FIG. 5B, there is shown a functional block diagram of an alternative implantable device 50'. The device 50' is in most respects the same as, or similar to, the device 50 shown in FIG. 5A. That is, the device includes an hermetically-sealed portion 54' wherein desired electronic circuitry is housed, including a power rectifier circuit 60' and a line interface circuit 62'. Other circuits, represented generically as the block 80, are coupled to the line interface circuit 62'. Such other circuits 80 may include, e.g., an I/F converter or other type of converter, a sensor, a stimulator, a counter, a microprocessor, and/or other circuits as needed to control and perform a desired stimulation or sensing function.

Like the device 50 of FIG. 5A, the device 50' of FIG. 5B includes a pair of feed through terminals 53' and 55' through which a LINE 1 and a LINE 2 connection may be respectively made between external (non-hermetically sealed) input terminal pads 13' and 15' and the hermetically sealed power rectifier circuit 60' and line interface circuit 62'. Unlike the device 50 of FIG. 5A, the device 50' of FIG. 5B includes output terminal pads 17' and 19' for LINE 1 and LINE 2 that are connected directly to the input terminal pads 13' and 15', respectively, without the connection passing through the hermetically sealed portion 54' of the device. As such, the configuration of the device 50' illustrated in FIG. 5B is better suited for applications where the sensor/stimulator devices in the daisy chain do not have to be lined up in serial or lead-like fashion (as suggested, e.g., by the devices 18a, 18b . . . 18n in FIG. 3), but wherein each device 50' of the chain may be fanned out and located or positioned at varying locations relative to the other devices in the chain.

Next, with reference to FIG. 5C, there is shown a functional block diagram of a sensor stimulator device 50". The device 50" is, in many respects, similar to the device 50 shown in FIG. 5A, but as is evident from FIG. 5C, the device 50" includes additional circuit functions that allow a wide variety of different sensor and/or stimulator functions to be provided. With the exception of stimulating electrodes 82 and 83, and portions of one or more of the sensors 53a, 53b, 53c, . . . 53n, all of the elements shown in FIG. 5C are included in an hermetically-sealed portion of the device 50".

Like the device 50 of FIG. 5A, the device 50" of FIG. 5C includes a power rectifier circuit 60" and a line interface circuit 62", each of which is connected to input/output LINE 1 and LINE 2 conductors. These LINE 1 and LINE 2 conductors are connected through appropriate feed-through elements (not shown) to appropriate pads (also not shown in FIG. 5C, but which are the same as or similar to the input/output pads 13, 15, 17 and 19 of FIG. 5A, or input/output pads 13', 15', 17' or 19' shown in FIG. 5B). The power rectifier circuit 60" and the line interface circuit 62" serve the same function as, and may be the same as or similar to, the power rectifier circuit 60 and line interface circuit 62 described or referenced above in connection with FIG. 5A. Also, like or similar to the device 50 of FIG. 5A, the device 50" shown in FIG. 5C may include a voltage generator circuit 78" that generates a $V_{REF}$ and $V_{BIAS}$ signal used by various other circuits within the device 50".

Unlike the device 50 of FIG. 5A, which includes a single sensor 52, the device 50" of FIG. 5C includes multiple sensors 53a, 53b, 53c, 53d, . . . 53n. Each of these sensors may be configured to sense a different parameter or substance, or all may be configured to sense the same parameter or substance. Alternatively, a first group of the sensors, e.g., sensors 53a and 53b, may be configured to sense the same parameter or substance; while a second group of the senors, e.g., sensors 53c, 53d, . . . 53n, may be configured to sense a different parameter or substance; while yet a third sensor or group of sensors, e.g., a sensor which generates a voltage $V_C$, may be configured to sense yet an additional parameter or substance. For example, sensors 53a and 53b may comprise strain gauges which measure movement of the tissue in which they are implanted; sensors 53c, 53d, . . . 53n may comprise glucose sensors that sense the glucose concentration of the tissue or fluids in which they are implanted, and the voltage $V_C$ may represent a voltage obtained from within the device 50" that represents a measure of the temperature of the device 50", and hence a measure (over time) of the temperature of the tissue in which the device 50" is implanted.

As shown in FIG. 5C, the sensors 53a and 53b each generate, as an output signal (having a magnitude that varies in some known fashion, e.g., linear, as a function of the parameter or substance being sensed) an output current $I_a$ and $I_b$, respectively. As required, the voltage $V_C$, which may represent a status condition or other parameter related to the device 50", may be applied to a voltage-to-current converter circuit 88, which circuit converts the sensed voltage $V_C$ to a corresponding current, $I_c$. The currents $I_a, I_b,$ and $I_c$ are all connected through an analog multiplexer circuit 90 to a first current-to-frequency (I/F$_0$) converter circuit 71a. The multiplexer 90 is controlled by a suitable control signal received over signal line 92 from state machine control logic 94.

The I/F$_0$ converter circuit 71a produces a variable frequency output signal (having a frequency that varies as a function of the selected input current $I_a, I_b,$ or $I_c$) which is directed to a first measurement counter 98a through a digital multiplexer 96. As shown in FIG. 5C, the digital multiplexer 96 may also select, under control of a control signal 95 received from the state machine control logic 94, the output frequency signal generated by a second current-to-frequency (I/F$_1$) converter circuit 71b, which I/F$_1$ converter circuit 71b receives an input current $I_1$ from sensor 53c. Thus, the first measurement counter 98a measures either the frequency of the output from the I/F$_0$ circuit 71a or the frequency of the output from the I/F$_1$ circuit 71b as controlled by the state machine control logic 94.

Other measurement counters 98b, . . . 98n may also be used to respectively measure the frequency signals generated by additional sensors 53d, . . . 53n. That is, sensor 53d generates an output current $I_2$ as a function of a sensed parameter or substance. This current 12 is applied to a third current-to-frequency (I/F$_2$) converter circuit 71c. The I/F$_2$ circuit 71c converts the current $I_2$ to a frequency signal, which frequency signal is applied to the measurement counter circuit 98b. In a similar manner, each other sensor that may be present in the device 50", up to sensor 53n, generates a corresponding output current as a function of a sensed parameter or substance. The current from each such sensor, including current $I_n$ from sensor 53n, is applied to a corresponding current-to-frequency converter circuit, up to an including an I/F$_n$ converter circuit 71n. Each such I/F converter circuit, up to the I/F$_n$ converter circuit 71n, converts its respective input current to a corresponding frequency signal, which frequency signal is then applied to a respective measurement counter circuit. Thus, for example, sensor 53n generates current $I_n$ as a function of a sensed parameter or substance, and applies this current $I_n$ to converter I/F$_n$, the frequency output signal of which is then applied to measurement counter 98n.

The output signals from each of the measurement counters 98a, 98b, . . . 98n, which output signals represent a digital measure of the parameter sensed by a corresponding sensor that is upstream from the measurement counter, are then selectively applied, through an output multiplexer circuit 100 to the line interface circuit 62". This selection is controlled by the state machine control logic 94 by way of a suitable control signal 97. The output signal selected by the multiplexer 100 thus comprises output data (referred to in FIG. 5C as "DATA OUT") that is applied to the LINE 1 and LINE 2 conductors of the two-conductor cable (or connecting bus) that connects each of the implantable devices 50" to a suitable controller 20. Thus, this output data may be transferred to the controller 20 over the LINE 1/LINE 2 conductors in the manner described below.

As described above, it is thus seen that the device 50" allows multiple sensors 53a, 53b, . . . 53n, to sense an appropriate parameter, substance, or condition, convert such sensed parameter, substance or condition to first a frequency signal, and second to a digital signal, which digital signal may then be selectively passed on to other devices, e.g., a remote controller 20, or another device 50, coupled to the LINE 1/LINE 2 conductors. Advantageously, through the use of the multiplexers 90, 96 and 100, each of which is controlled by suitable state machine control logic 94, the frequency at which a given sensor is sampled can be controlled in a desired manner. For example, as suggested by the configuration shown in FIG. 5C, it is seen that sensors 53d . . . 53n may be sampled at a rate controlled by output multiplexer 100. Sensor 53c may similarly be sampled at a rate controlled by output multiplexer 100 and multiplexer 96; and sensors 53a and 53b, as well as status voltage $V_c$, may be sampled at a rate controlled by output multiplexer 100, multiplexer 96 and multiplexer 90.

It is to be emphasized that the particular configuration (shown in FIG. 5C) of using multiple sensors and multiplexers is only exemplary, not limiting. It is intended that any configuration of an implantable, daisy-chainable device that allows one or more, e.g., multiple, sensors to be employed within the device, with the data sensed by each sensor being convertible to an appropriate form and transferrable back through a suitable line interface circuit to the LINE 1/LINE 2 conductors, being included be included within the scope of the invention.

Still referring to FIG. 5C, it is seen that the device 50" further includes a stimulator circuit 86. The stimulator circuit 86 is controlled by the state machine control logic 94. The stimulator circuit 86 generates appropriate electrical stimulation pulses, applied across one or more electrodes 82 and/or 83. These electrodes 82 and/or 83 are connected to the stimulator circuit 86 through conductors that pass through an appropriate feed-through terminal, or seal 84, thereby allowing at least one of the electrodes to be in the non-hermetically sealed portion of the device 50". The design of the stimulator circuit 86 may be conventional, e.g., as is commonly used in the cochlear stimulation art, see. e.g. U.S. Pat. No. 5,603,726 (incorporated herein by reference), the cardiac tissue stimulation art, the neural stimulation art, and/or the pain-relief stimulation art.

The state machine control logic 94 may likewise be of conventional design, appropriate for the low power constraints applied to all of the circuitry within the device 50". It is the function of the state machine control logic 94 to generate control signals that control the operation of the stimulator circuit 86, as well as the sampling and data conversion associated with each of the various sensors 53a, 53b, . . . 53n, all as controlled by and in synchrony with DATA-IN signals and a clock (CLK) signal received from the line interface circuit 62". In its simplest form, the control logic 94 may comprise simply a flip-flop or two, and associated logic gates, which receive the DATA-IN and CLK signals and use such signals to steer or control the flip flop(s) to toggle between, or cycle through, various operating states. In each state, appropriate control signals are generated by the control logic to cause a specified sensor to be sampled, and/or a stimulation pulse to be generated. As required, reset signals are also generated in the various states in order to reset the various counter circuits. Additionally, a power-on-reset circuit 102 may be coupled to the state machine control logic 94 to assure that the control logic 94 comes up in a desired state, or operating mode, each time power is applied to the device 50". The details of the state machine control logic are not critical for purposes of the present invention. Those of skill in the art can readily fashion appropriate state machine control logic to accomplish a desired operating performance for the device 50".

It should also be pointed out that any circuitry which accomplishes the function of the state machine control logic 94 could be used in lieu of, or as a supplement to, the conventional state machine control logic described above. Such circuitry includes, for example, a low power microprocessor programmed with an operating program stored in read-only memory (ROM).

Further, it is noted that inclusion of a stimulator circuit 86, and corresponding stimulation electrodes 82 and/or 83, within the implantable device 50" should be viewed as an option, not a requirement.

That is, for many applications, all that the daisy-chainable implantable device 50" need do is to sense one or more parameters or substances, without the need to provide stimulation. For such applications, the stimulation function may thus be omitted.

The current-to-frequency converter circuits 71a, 71b, . . . 71n may each be substantially as is described in the previously-referenced patent application Ser. No. 08/928, 868 (incorporated herein by reference) entitled LOW POWER CURRENT-TO-FREQUENCY CONVERTER CIRCUIT FIT USE IN IMPLANTABLE SENSORS.

The counter circuits 98a, 98b, . . . 98n, as well as the multiplexer circuits 90, 96 and 100, may all be of conventional design, utilizing, e.g., low power CMOS integrated circuits.

Turning back momentarily to FIG. 2, where a plurality of implantable, daisy-chainable sensor/stimulator devices 18a, 18b . . . 18n made in accordance with the present invention are shown connected in tandem, it is noted that a key feature of the present invention is the ability of the controller 20 to provide operating power to, and to individually send control data to, as well as receive data from, each of the devices 18 that are connected to the controller over the same two conductors 14 and 16. The preferred manner in which such powering and individual addressing is done is next explained in connection with FIGS. 6, 7 and 8.

Figure 6:
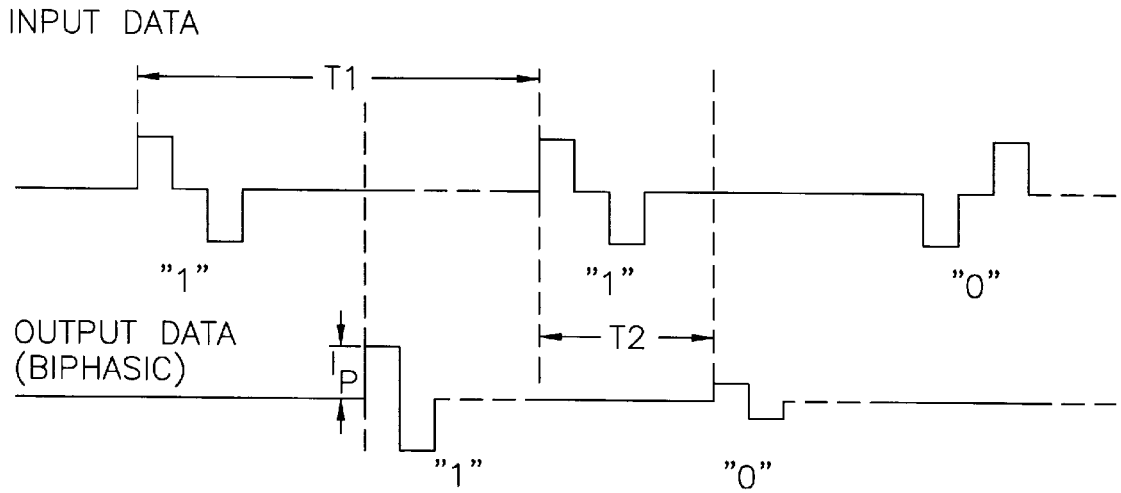
FIG. 6 is a timing diagram that illustrates input and output data sent to and received from a daisy-chainable device of the type shown in FIG. 5A, 5B or 5C.

FIG. 6 illustrates a timing diagram that shows the preferred relationship between input data (top waveform) sent to the implantable devices and output data (bottom waveform) received from the implantable devices, as such data would appear on the two LINE 1/LINE 2 conductors that connect all of the devices together. In FIG. 6, it is assumed that time is the horizontal axis, whereas amplitude is the vertical axis. It is also noted that the waveforms shown in FIG. 6 represent current waveform pulses.

As seen in FIG. 6, the preferred form for the input data is biphasic pulses. Each biphasic pulse comprises a first current pulse of a first polarity, followed by a second current pulse of the same magnitude of the opposite polarity. Thus, the net current for each biphasic pulse is preferably zero, with the positive current pulse effectively balancing out the negative current pulse. The typical widths of the current pulses are from 1 to 100 microseconds ($\mu$sec), with the magnitude of each current pulse typically ranging from 10 to 1000 microamps ($\mu$amp). A binary "1" may be represented by a biphasic pulse of one phase, e.g., a positive current pulse followed by a negative current pulse; while a binary "0" may be represented by a biphasic pulse of the opposite phase, e.g., a negative pulse followed by a positive pulse. Thus, as shown in FIG. 6, a binary "1" may be represented as a positive current pulse followed by a negative current pulse, while a binary "0" is represented by a negative current pulse followed by a positive current pulse.

As further seen in FIG. 6, there may be an "off time", e.g., of 0 (zero) to 10 $\mu$sec, between the two current pulses of each biphasic pulse, but such off time is not always necessary (hence, as indicated, it may be reduced to zero). A prescribed time increment T1 separates one input data biphasic current pulse from the next input data biphasic current pulse.

As also seen in FIG. 6, the preferred form for the output data is also a biphasic pulse, amplitude modulated (or preferably ON/OFF modulated) as a function of whether the output data is a binary "1" or "0". In the preferred embodiment, the peak amplitude of the output data pulse for a binary "1" is $I_P$, while the peak amplitude of the output data pulse for a binary "0" is zero. Thus, in this preferred ON/OFF modulation scheme, the presence of an output data pulse represents a binary "1" and the absence of an output data pulse represents a binary "0". Output data pulses are inserted in the data stream appearing on the LINE 1/LINE 2 conductors pulses at a specified time T2 from the input data pulse so as to fall between the input data pulses, in a time-division multiplexed manner. Although the preferred form of the output data pulses is a biphasic pulse (to achieve current balancing), it is noted that in some instances a monophasic pulse at time T2 (and with amplitude of $I_P$ or zero) may be used.

Figure 7:
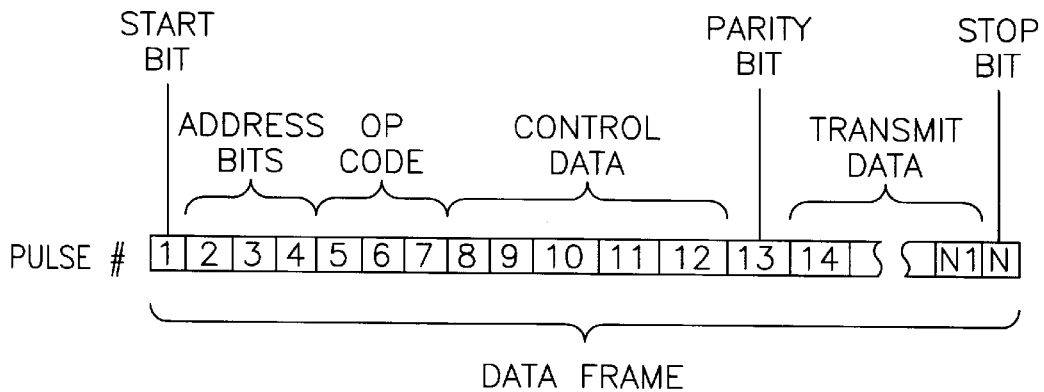
FIG. 7 illustrates a data frame used to communicate with the implantable device of the present invention when serially connected in a daisy chain.
Figure 8:
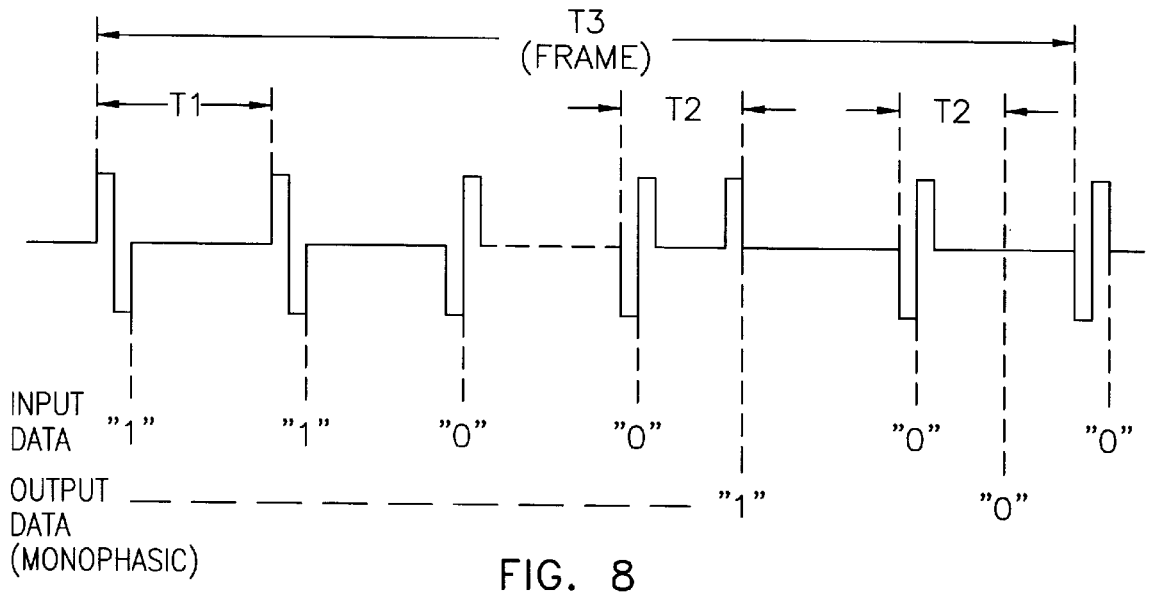
FIG. 8 is a timing diagram that illustrates time multiplexed input and output data within a data frame as it appears on the two-conductor bus connecting a plurality of daisy-chainable devices of the type shown in FIG. 5A, 5B or 5C.

As shown in FIGS. 7 and 8, the input data sent over the LINE 1/LINE 2 conductors by the controller is divided into data frames of length T3. Note that the data frame shown in FIG. 7 represents a different data frame than that which is shown in FIG. 8. Within each data frame, N bits of data are found, where N is an integer typically ranging from 4 to 64. FIG. 7 illustrates a generalized data frame of N bits; while FIG. 8 illustrates a data frame of six bits.

A representative assignment of the data bits included in a generalized data frame is illustrated in FIG. 7. As shown in FIG. 7, the first bit of the data frame is a start bit, followed by three bits (bits 2, 3 and 4) that comprise address bits. Bits 5, 6 and 7 comprise an operation code (op code) that define an operation (e.g., one of eight operations) that the addressed device is to perform. Bits 8–12 then define particular control parameters associated with the operation that is to be carried out, e.g., the amplitude of a stimulation pulse, or the particular sensor(s) from which data is to be gathered, etc. Bit 13 comprises a parity bit. Bits 14 through N−1 comprise transmit data, followed by the Nth bit, which is a stop bit or end bit of the data frame.

The transmit data bits, in one embodiment, effectively define time windows within the data frame during which data being sent (or transmitted) from a given implantable device to the controller is to be inserted in the data frame. For example, the controller may be set up to recognize that output data appearing T2 seconds after the 13th input data pulse (i.e., during Bit 13) corresponds to data sent by a specific one of the devices in the daisy chain. In this manner, some data from each of the implantable devices in the chain may be received during each data frame. Alternatively, other schemes may be used to keep track of which output data appearing on the LINE 1/LINE 2 conductors belongs to which devices. For example, all of the devices but one may be effectively shut down insofar as sending output data is concerned until all the needed data from that one enabled device has been obtained. This allows data to be received much faster from a given device, but at the expense of not receiving data from the other devices until the transmission is complete.

Because the input data comprises biphasic pulses that occur at a regular interval or rate (e.g., every T1 seconds), the energy contained in such pulses may be utilized to provide the operating power for the circuits contained within the device 50". Such is accomplished using the rectifier circuit 60, 60' or 60" (FIGS. 5A, 5B or 5C). A preferred rectifier circuit is described in the above-referenced co-pending patent application Ser. No. 08/928,871 (incorporated herein by reference) entitled LOW POWER RECTIFIER CIRCUIT.

Figure 9:
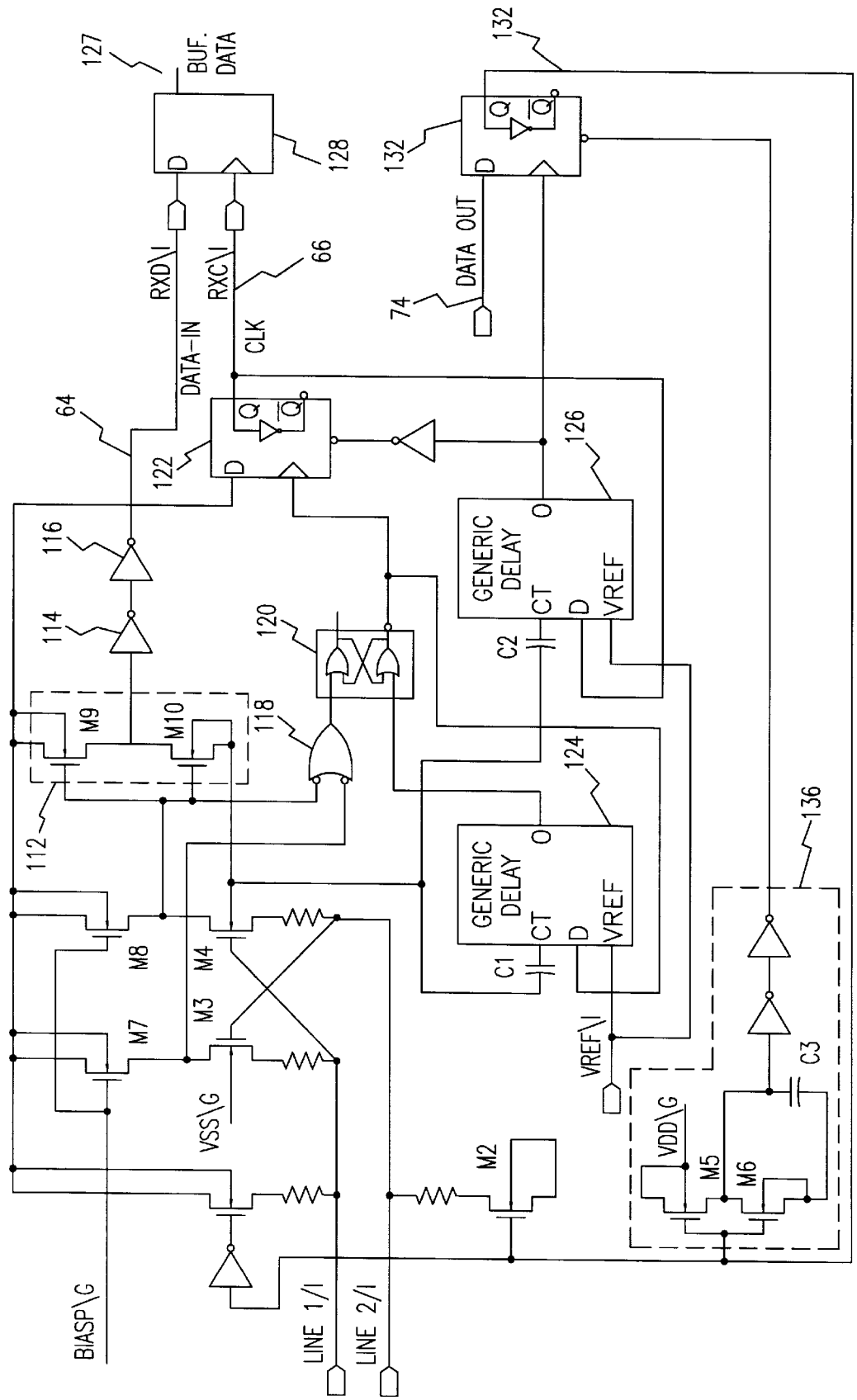
FIG. 9 shows a representative schematic diagram of a typical line interface circuit that may be used as part of the daisy-chainable implantable devices of the type shown in FIGS. 5A, 5B or 5C.

The input and output data pulses of the type shown in FIGS. 6 and 8 are generated by the line interface circuit 62, 62' or 62" (FIGS. 5A, 5B or 5C). A schematic diagram of a representative line interface circuit is shown in FIG. 9. The transistor elements included in the circuit of FIG. 9 are of the P-MOS FET or N-MOS FET type. Representative sizes of such transistor elements are listed in Table 1. The N-MOS FET and P-MOS FET dimensions shown in Table 1 relate to the relative size of each transistor as it is formed on the IC substrate. More particularly, an N-MOS FET, for example, having a size of "5/10" means that the width of the source to drain channel is 5 microns (where "micron" means one micrometer, also written as 1 $\mu$m, or $1\times10^{-6}$ meters), and the length of the channel is 10 microns. This type of characterization (by dimension or size) of the various N-MOS FET and P-MOS FET transistors used within an IC is known and understood by those of skill in the semiconductor processing art. Advantageously, by selectively controlling the size (dimensions) of such transistors during the IC processing steps, the performance of the N-MOS and P-MOS FET transistors can be controlled or tailored for the specific design for which the transistor is used. Thus a relatively "long" N-MOS FET, having a size of, e.g., 5/10, may exhibit a higher turn-on resistance (and hence a slower turn on time) than would, e.g., a relatively "short" N-MOS FET, having a size of 4/4.

TABLE 1

Representative Sizes of Transistor Elements of FIG. 9

| Device | Type | Size (W/L $\mu$m) |
| --- | --- | --- |
| M1 | P-MOS | 100/0.8 |
| M2 | N-MOS | 50/0.8 |
| M3 | N-MOS | 10/0.8 |
| M4 | N-MOS | 10/0.8 |
| M5 | P-MOS | 2.4/0.8 |
| M6 | N-MOS | 2.4/200 |
| M7 | P-MOS | 4/0.8 |
| M8 | P-MOS | 4/0.8 |
| M9 | P-MOS | 4/0.8 |
| M10 | N-MOS | 2.4/5.4 |

The particular line interface circuit shown in FIG. 9 receives biphasic pulses from and sends monophasic pulses back to the controller 20 (FIG. 2). The operation of the circuit shown in FIG. 9 should be self-evident to those of skill in the art. The following explanation provides an overview of such operation.

The biphasic pulses appearing on the LINE 1/LINE 2 conductors are effectively pulse pairs, one pulse of the pair being positive and the other being negative, with the polarity of the first pulse determining whether the pulse represents a binary "1" or a binary "0". The LINE 1/LINE 2 conductors are connected to CMOS switches M3 and M4 such when LINE 1 goes high, it switches on M4 and switches off M3. Switching on M4 pulls down the level at the drain of M4 for the duration of the pulse. Switching M3 off makes the drain of M3 go high. The low pulse at the drain of M4 passes through three inverters 112, 114 and 116 and appears as a high data pulse at the DATA-IN signal line 64, having the same pulse width as the incoming pulse. Thus, incoming positive pulses on LINE 1 are passed through as positive pulses on the DATA-IN line 64.

In a similar fashion, negative pulses on LINE 1 cause M3 to switch ON and M4 to switch off. With M4 switched off, the drain of M4 is pulled high, and this high level passes through inverters 112, 114 and 116 to become a low level data pulse at the DATA-IN signal line 64 having the same pulse width as the incoming negative pulse. Thus, incoming negative pulses on LINE 1 are passed through as low pulses on the DATA-IN line 64.

The clock signal, on signal line 66, is generated by a D-flip-flop 122, as controlled (or clocked by) the rising edge of the Q* output of a NOR latch 120.

The NOR latch 120 is reset by gate 118, causing the Q* output of latch 120 to rise, whenever either one of the M3 or M4 switches are turned on, which occurs whenever an input pulse of either polarity is received. Having the NOR latch 120 reset, thereby causing its Q* output to rise from a low level to a high level, causes two events to happen: (1) a first timer circuit 124 starts its timing cycle; and (2) the D flip-flop 122 is clocked, causing its Q output (attached to signal line 66) to be set to a high level. The rising edge of the signal on signal line 66 further causes a second timer circuit 126 to be triggered. Representative times for the first and second timers are 152 microseconds (μsec) and 44 μsec, respectively. Thus, as soon as an input pulse is received, positive or negative, both the first and second timers start to time out.

For so long as the first timer circuit 124 is timing out, e.g., for 152 μsec following an input pulse, it locks the NOR latch 120, making it immune to any further signals received from the M3 or M4 switches (i.e., making it immune to any line activity appearing on the LINE 1/LINE 2 signal lines). Line activity during this immune time typically includes the second line pulse of the biphasic pulse pair, any reply pulse that may be deliberately placed on the LINE 1/LINE 2 signal lines (as explained below), or noise. As soon as the first timer 124 times out, the NOR latch 120 is unlocked, making it responsive to the next line activity that occurs, e.g., the next biphasic data pulse, representing the next data bit of the data frame.

When the second timer 126 times out, e.g., at 44 μsec after receipt of an incoming pulse, the Q output of the second timer 126 goes high, causing the D flip-flop 122 to reset, thereby causing the clock signal on signal line 66 go low. The clock signal on signal line 66 remains low until the D flip-flop 122 is again clocked high by the NOR latch 120 upon receipt of the next input pulse over the LINE 1/LINE 2 conductors (after expiration of the 152 μsec immune period set by the first timer 124). Thus, the clock signal CLK (on signal line 66) comprises a signal that goes high upon receipt of the first pulse over the LINE 1/LINE 2 conductors, remains high for the second timer period, e.g., 44 μsec, and then goes low and remains low until receipt of the next input pulse over the LINE 1/LINE 2 conductors after expiration of the first timer period (e.g., 152 μsec). For this reason, the data transmission cycle from the remote controller 20 (FIG. 2) should not be shorter than the longest possible time of the first timer 124, taking into account variations in the timer period as a result of process variations. For example, assuming a nominal first timer value of 154 μsec, a safe value for the data transmission cycle is about 244 μsec, which allows for about a ±52% variation in the first timer period.

Note that there is a shorter propagation delay from receipt of a pulse on the LINE 1/LINE 2 input lines to the DATA-IN line 64 than to the CLK line 66. This is important in forming a buffered data line 127 using another D flip-flop 128. Such a buffered data line 127 is created by connecting the DATA-IN line 64 to the D-input of the D flip-flop 128, while connecting the clock input of the D flip-flop 128 to the CLK line 66. By making the propagation delay to the DATA-IN line 64 be shorter than the propagation delay to the CLK line 66, the D flip-flop 128 will always capture and hold the correct data on the DATA-IN line at the time of the clock transition. Thus, whenever a positive pulse is first received on LINE 1 relative to LINE 2 (i.e., whenever the first pulse of the biphasic pulse pair is positive), causing the DATA-IN line to go high for the duration of the pulse as explained above, the D flip-flop 128 captures such event as a high level, causing the buffered data line 127 to latch high. Similarly, whenever a negative pulse is first received on LINE 1 relative to LINE 2 (i.e., whenever the first pulse of the biphasic pulse pair is negative), causing the DATA-IN line to go low for the duration of the pulse as explained above, the D flip-flop 128 captures such event as a low level, causing the buffered data line 127 to latch low.

Note that the D flip-flop 128 need not be included as part of the line interface circuit 62 (although it could be), but rather is usually included in the state machine logic 94, or other processing circuitry, that receives and processes the incoming data.

Output data that is to be placed on the LINE 1/LINE 2 conductors at a time T2 after receipt of an input data pulse, is applied to the DATA OUT signal line 74. Such data is then clocked into D flip-flop 132, causing the data (a low or a high) to appear on signal line 134, at the end of the 44 μsec period set by the second timer 126. If the output data is a "1", i.e., a high level, such action triggers a third timer circuit 136, which times out after a prescribed time period, e.g., 1 sec. The timing out of the third timer circuit 136 resets the D flip-flop 132, thereby causing the signal line 134 to go low, thus forming an output data pulse of approximately 1 μsec width on the signal line 134. Such output data pulse is then inserted on the LINE 1/LINE 2 conductors by action of the complimentary switches M1 and M2, both of which are turned ON by the 1 μsec output data pulse, with M1 pulling LINE 1 high, and M2 pulling LINE 2 low, for the duration of the output data pulse, e.g., 1 μsec. Thus, in this manner, the output data pulse appears on LINE 1/LINE 2 at a time T2, as shown, e.g., in FIGS. 6 and 8.

If the output data applied to the DATA OUT line 74 is a "0", i.e., a low level, a low level is clocked in to the D flip-flop 132. This means there is no change on signal line 134, the third timer circuit 136 is not triggered, and the M1 and M2 triggers are not turned ON. Thus, there is no data pulse inserted on LINE 1/LINE 2, and the absence of such data pulse signifies the output data is a "0". By having an output data "0" be represented by the absence of an output pulse saves operating power of the device. Saving operating power is always an important consideration for the type of implantable sensor/stimulator devices described herein.

The 1 μsec time period set by the timer circuit 136 is achieved, in the embodiment shown in FIG. 9, by designing an inverter circuit using complementary transistors M5 and M6, where the NFET (M6) of the pair is designed to have long dimensions, as seen in Table 1. Such long dimensions, in combination with the capacitance of capacitor C3 (nominally 3 picofarads), produces the desired 1 μsec delay. The typical dimensions of the other transistors, M1, M2, M3, M4 and M5 included in the circuit of FIG. 9 are also shown in Table 1.

As described above, it is thus seen that the present invention provides a means whereby implantable sensors or stimulators may be daisy chained together over a common power/data bus using a minimum number of connecting conductors, e.g., two, and wherein each individual device connected in the daisy chain is individually addressable from a common controller unit connected by way of the common power/data bus to each of the implantable devices.

As also described above, it is seen that the invention provides individual implantable sensors and/or stimulators that can transmit and/or receive power and data signals over a minimum number of signal lines connected therebetween.

As further described above, it is seen that each such implantable sensor/stimulator device of the invention has an hermetically sealed part and a non-hermetically sealed part, with electrical feed-through means for making electrical connections between the hermetically sealed part and the non-hermetically sealed part, and wherein the hermetically sealed part encompasses electrical circuits for operating and controlling the device, and further wherein the non-hermetically sealed part includes a sensor for sensing a condition or substance to which the device is exposed, electrical terminals or pads to which connecting conductors may be connected, and/or electrodes through which stimulating current pulses may be applied to surrounding tissue or body fluids.

While the invention herein disclosed has been described by means of specific embodiments and applications thereof, numerous modifications and variations could be made thereto by those skilled in the art without departing from the scope of the invention set forth in the claims.

What is claimed is:

1. An implantable sensor/stimulator comprising:

a carrier having first and second pads thereon;

first and second line conductors;

wherein said first and second line conductors attached to said first and second carrier pads, respectively;

a rectifier circuit carried by said carrier and connected to the first and second pads; said rectifier circuit including means for generatingy an operating voltage from biphasic pulses applied across said first and second pads;

a line interface circuit carried by said carrier and connected to the first and second pads, said line interface circuit including detecting means for serially detecting whether the biphasic pulses applied across said first and second pads are a first phase or a second phase, a first phase corresponding to a received data bit representing a binary "1", and a second phase corresponding to a received data bit representing a binary "0", whereby an input data stream is received by the line interface circuit from biphasic data pulses applied between the first and second line conductors, and hence, between the first and second pads attached to the first and second line conductors, and transmission means for serially applying a monophasic pulse having a first or second amplitude across said first and second pads at a time in-between when the biphasic pulses are applied across the first and second pads, a first amplitude of the monophasic pulse representing a binary "1", and a second amplitude of the monophasic pulse representing a binary "0", whereby an output data stream may be transmitted by the line interface circuit onto the first and second pads, and hence, onto the first and second line conductors attached to the first and second pads;

a sensor carried by said carrier, said sensor having means for sensing a specified parameter or substance and means for generating an analog output signal that varies as a function of how much of the specified parameter or substance is sensed;

a converter circuit carried by said carrier that converts the analog output signal from said sensor to a digital sensor signal comprised of a multiplicity of respective bits;

state machine means carried by said carrier for defining address data corresponding to said implantable sensor/stimulator, and for receiving detected data from the detection means and determining if said detected data corresponds to the defined address data of said implantable sensor/stimulator, and if so, responding thereto by applying the digital sensor signal to the transmission means of the line interface circuit, wherein the respective bits of the digital sensor signal function as the output data stream that is transmitted by the line interface circuit onto the first and second pads, and hence, onto the first and second line conductors attached to the first and second pads; and means for hermetically sealing said rectifier circuit, line interface circuit, converter circuit, and state machine means.

2. The implantable sensor/stimulator of claim 1 wherein the analog output signal generated by the sensor comprises an electrical current, and wherein said converter circuit comprises:

a current-to-frequency converter circuit which includes means for converting the electrical current from said sensor to a variable frequency pulsed signal, the frequency of the variable frequency pulsed signal being a function of the magnitude of the electrical current generated by the sensor; and a counter circuit that counts the pulses of the variable frequency pulsed signal over a specified period of time to form a count signal, the count signal thereby comprising said digital sensor signal, said digital sensor signal providing a measure of the specified parameter or substance sensed by the sensor.

3. The implantable sensor/stimulator of claim 1 further including a stimulator circuit and at least one pair of electrodes connected to said stimulator circuit, said stimulator circuit being coupled to the state machine means and having means responsive to command data received by the state machine means from the detecting means of the line interface circuit for generating a stimulation pulse that is applied to the at least one pair of electrodes.

4. The implantable sensor/stimulator of claim 1 further comprising a plurality of sensors, each generating an analog electrical current as a function of a specified sensed parameter, and multiplexer means for selectively connecting each of the plurality of sensors to a corresponding converter circuit as controlled by command data received via the line interface circuit.

5. An implantable medical device comprising:

an hermetically sealed part containing electrical circuitry;

said electrical circuitry performing a medical function selected from the group consisting of medical electrical stimulation, medical electrically mediated stimulation, medical electrical sensing, the combination medical electrical stimulation and electrical medical sensing, medical electrical-mediated release of medication at an implant site and medical electrical-mediated release of medication at a non-implant site;

a non-hermetically sealed part, the non-hermetically sealed part including a first pair of terminals and a second pair of terminals, wherein the first pair of terminals are electrically connected to the second pair of terminals; and feed-through means for making electrical contact between each terminal of the first pair and second pair of terminals and a respective portion of the electrical circuitry within the hermetically sealed part;

wherein said first pair of terminals comprises a means for applying electrical power and data to the electrical circuitry within the hermetically sealed part, as well as a means for receiving data from the electrical circuitry within the hermetically sealed part, and said second pair of terminals similarly comprises a means for passing the electrical power and data received on the first pair of terminals to a corresponding first pair of terminals of another implantable medical device, whereby a plurality of said implantable medical devices may be daisy-chained together by connecting a pair of conductors between the second pair of terminals of one implantable medical device and the first pair of terminals of another implantable medical device;

said implantable medical device wherein the implantable medical device comprises an implantable sensor that senses a parameter associated with living tissue within which the medical device is implanted, and wherein the hermetically sealed part of the implantable medical device includes electronic sensor circuitry for operating and monitoring said sensor, and further wherein the electronic circuitry receives electrical signals through the faced-through means that power and control the operation of said sensor;

said medical device wherein the implantable sensor generates an electrical current having a magnitude that varies as a function of the sensed parameter, and wherein the electronic sensor comprises a rectifier circuit connected to the first pair of terminals, said rectifier circuit including means for generating an operating voltage from an electrical signal applied across said first pair of terminals;

a line interface circuit also connected to the first pair of terminals for detecting input data within the electrical signal applied across said first pair of terminals, and for allowing output data to be placed within the electrical signal appearing across said first and second pair of terminals;

current-to-frequency converter means coupled to the sensor for converting the electrical current generated by the sensor to a signal comprising a stream of electrical pulses, wherein the time interval between adjacent pulses of said stream of electrical pulses varies as a function of the magnitude of the electrical current; and a counter circuit for counting the number of pulses that occur within the stream of electrical pulses within a set time period, the number of pulses thus counted providing a measure of the electrical current, the count derived by said counter circuit after said set time period comprising output data that is coupled to said line interface circuit.

6. A chain of serially-connected electronic devices adapted for implantation in living tissue comprising:

a plurality of substantially identical electronic devices, each electronic device including a first pair of terminals, a second pair of terminals, means for receiving an input pulsed data-stream signal over the first pair of terminals, means for performing a medical function selected from the group consisting of medical electronic stimulation, medical electronically mediated stimulation, medical electronic sensing, the combination medical electronic stimulation and electronic medical sensing, medical electronic-mediated release of medication at an implant site and medical electronic-mediated release of medication at a non-implant site, and means for applying output pulses to the first pair of terminals representative of the specified function performed so that the output pulses are interleaved between pulses of the input pulsed data-stream signal;

a control circuit having a first line terminal and a second line terminal, means for generating the input pulsed data-stream signal and applying said input pulsed data-stream signal between the first line terminal and the second line terminal, and means for detecting any output pulses appearing between pulses of the input pulsed data-stream;

a first line conductor connected between the first line terminal of the control circuit and a first terminal of the first pair of terminals of a first electronic device, and a second line conductor connected between the second line terminal of the control circuit and a second terminal of the first pair of terminals of the first electronic device; and for each additional electronic device included in the chain of implantable serially-connected electronic devices, wherein an electronic device in the chain that is closest to the control circuit comprising a forward electronic device, and an electronic device in the chain that is next closest to the control circuit comprising a rearward electronic device a signal conductor connected between a first terminal of the second pair of terminals of the forward electronic device and a first terminal of the first pair of terminals of the rearward electronic device, and a return conductor connected between a second terminal of the second pair of terminals of the forward electronic device and a second terminal of the first pair of terminals of the rearward electronic device;

whereby the first electronic device is connected to the control circuit with just two conductors, and each rearward electronic device in the chain of electronic devices is also coupled to the forward electronic device with just two conductors;

said chain of implantable electronic devices wherein the specified function performed by each of the plurality of electronic devices comprises sensing and measuring a parameter associated with the living tissue within which the chain of devices is implanted;

said chain of implantable electronic devices wherein the input pulsed data stream signal generated by the control circuit comprises a train of biphasic pulses, with each biphasic pulse in the train of pulses comprising a negative pulse followed by a positive pulse to represent one binary state, and a positive pulse followed by a negative pulse to represent the other binary state, and wherein each biphasic pulse is separated from an adjacent biphasic pulse in the train of biphasic pulses by a time period T1, and further wherein the train of biphasic pulses is applied to the first pair of terminals of each electronic device in the chain.

7. The chain of implantable electronic devices as set forth in claim 6 wherein the train of biphasic pulses comprises a sequence of biphasic pulses grouped in a frame, with each biphasic pulse representing a data bit, wherein a first group of data bits within the frame comprises an address, a second group of data bits within the frame comprises an operational code, and a third group of data bits within the frame comprises data.

8. The chain of implantable electronic devices as set forth in claim 7 wherein the third group of data bits includes a first subgroup of data bits representing op code bits, and a second subgroup of data bits representing transmitted data.

9. The chain of implantable electronic devices as set forth in claim 8 wherein the data frame further includes at least one additional biphasic pulse representing a parity bit.

10. The chain of implantable electronic devices as set forth in claim 8 wherein the data frame further includes a first biphasic pulse representing a start bit, and a last biphasic pulse representing a stop bit.

11. The chain of implantable electronic devices as set forth in claim 6 wherein the output pulses generated by each electronic device comprise output pulses having a variable amplitude, and wherein each electronic device includes means for interleaving the output pulses in the data stream of biphasic pulses at a time period T2 from a prior biphasic pulse, where T2 is less than T1.

12. The chain of implantable electronic devices as set forth in claim 11 wherein the output pulses assume a first amplitude to represent a first binary state, and a second amplitude to represent a second binary state.

13. The chain of implantable electronic devices as set forth in claim 11 wherein the output pulses assume a first amplitude to represent a first binary state, and are absent, i.e., assume a zero amplitude, to represent a second binary state.

14. The chain of implantable electronic devices as set forth in claim 11 wherein the output pulses comprise monophasic pulses.

15. The chain of implantable electronic devices as set forth in claim 11 wherein the output pulses comprise biphasic pulses.

16. A method of sending power and control data to, and receiving transmit data from, a plurality of implantable medical devices, each connected to a two-conductor cable, comprising:

(a) generating a biphasic pulse train of biphasic pulses at a regular repetition rate of F1 pulses per second (pps), wherein each biphasic pulse in the pulse train has a width $T_W$ and is separated from an adjacent pulse in the pulse train by a time separation distance of T1, where $T_W$ is <<T1, and T1=1/F1;

(b) modulating the pulses of the pulse train to represent data bits, wherein a biphasic pulse which goes positive first and then negative comprises a first binary state, e.g., a logical one, and wherein a biphasic pulse which goes negative first and then positive comprises a second binary state, e.g., a logical zero;

(c) arranging the biphasic pulses of the pulse train in data frames of N data bits each, wherein a first subset of the N data bits comprise address bits, a second subset of the N data bits comprise an operational code, a third subset of the N data bits comprise data;

(d) applying the data frames to the two-conductor cable so that the data frames are received by each of the plurality of implantable medical devices connected to the two-conductor cable;

(e) receiving and processing the data frames within each medical device by:
  (1) splitting the received biphasic pulses into first and second signal paths,
  (2) rectifying and filtering the biphasic pulses received in the first signal path to create an operating voltage used to operate the medical device,
  (3) demodulating the address bits received in the second signal path of each data frame to determine if the address bits match a predetermined address stored in the medical device, and
  (4) if the address bits match the predetermined address, demodulating the operational code and data received in the second data path; and (f) sending transmitted data from a medical device for which a match exists between the address bits received and the predetermined address by:
  (1) generating an output data pulse having a width <<T1, the output data pulse having a first amplitude, e.g., a maximum amplitude, to represent a first binary state, and a second amplitude, e.g., a minimum amplitude, to represent a second binary state, and
  (2) applying the output data pulse to the two-conductor cable at a time in the data frame that is inbetween the biphasic pulses of the N data bits that define a data frame.

17. The method of claim 16 wherein the first amplitude of step (f) (1) comprises a non-zero amplitude, and the second amplitude of step (f) (1) comprises a zero amplitude, whereby the presence of an output data pulse having a discernable amplitude at the time in the data frame that is inbetween the biphasic pulses of the data bits in the data frame represents the first binary state, and the absence of an output data pulse represents the second binary state.

* * * * *